United States Patent [19]
Boykin et al.

[11] Patent Number: 5,622,955
[45] Date of Patent: Apr. 22, 1997

[54] **METHODS OF TREATING *CRYPTOSPORIDIUM PARVUM***

[75] Inventors: David W. Boykin, Atlanta, Ga.; Christine C. Dykstra, Chapel Hill, N.C.; Richard R. Tidwell, Pittsboro, N.C.; James E. Hall, Chapel Hill, N.C.; W. David Wilson; Arvind Kumar, both of Atlanta, Ga.; Byron L. Blagburn, Auburn, Ala.

[73] Assignees: The University of North Carolina at Chapel Hill, Chapel Hill, N.C.; Georgia State University Research Foundation, Inc., Atlanta, Ga.; Auburn University, Auburn, Ala.

[21] Appl. No.: 456,164

[22] Filed: May 31, 1995

Related U.S. Application Data

[60] Division of Ser. No. 305,823, Sep. 13, 1994, Pat. No. 5,521,189, which is a continuation-in-part of Ser. No. 238,766, May 6, 1994.

[51] Int. Cl.$^6$ ............... A61K 31/505; C07D 239/26
[52] U.S. Cl. ............... 514/256; 514/269; 544/242; 544/296; 544/298; 544/322; 544/326
[58] Field of Search ............... 514/256, 269; 544/242, 298, 322, 326, 296

[56] References Cited

U.S. PATENT DOCUMENTS 5,521,189  5/1996  Boykin et al. ............... 514/256

FOREIGN PATENT DOCUMENTS 3319843A  6/1983  Germany ............... 544/242

OTHER PUBLICATIONS

B.P. Das et al; 1,4 Bis(4guanylphenylethyl)benzenes as Potential Antitrypanosomal Agents, *Journal of Pharmaceutical Sciences* 71: pp. 465–466 (1982).

B.P. Das et al; Synthesis and Antiprotozoal Activity of 2,5-Bis(4-guanylphenyl)furans, *Journal of Medicinal Chemistry* 20, pp. 531–536 (1977).

B.P. Das et al; Snythesis and Antiprotozoal Activity of 2,5-Bis(4-guanylphenyl)thiophenes and –pyrroles, *Journal of Medicinal Chemistry* 20, pp. 1219–1221 (1977).

B.P. Das et al; Synthesis and Antitrypanosomal Activity of Some Bis(4-guanylphenyl) Five-and Six-Membered Ring Heterocycles, *J. Med. Chem.* 23, pp. 578–581 (1980).

C. C. Dykstra et al; *Synthesis and Characterization of a Novel Series of Aromatic Dicationic Furans With DNA-Specific Fluorescence Properties*, pp. 1–7 (1994).

D.E. Rooney et al; Human Cytogenetics: A Practical Approach, ed. *IRL Press, Oxford University Press*, selected pages (1992).

*Primary Examiner*—Yogendra N. Gupta
*Attorney, Agent, or Firm*—Bell, Seltzer, Park & Gibson

[57] ABSTRACT

The present invention provides methods for treating *Cryptosporidium parvum* in a subject in need of such treatment. The methods comprises administering to the subject a compound of Formula I:

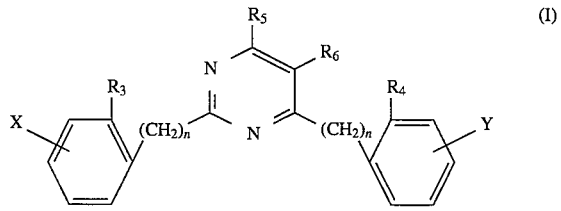

15 Claims, No Drawings

METHODS OF TREATING *CRYPTOSPORIDIUM PARVUM*

The present invention was made with Government support under Grant Number UO1-A1-3363 from the National Institutes of Health. The Government has certain rights this invention.

RELATED APPLICATIONS

This application is a divisional of U.S. patent application Ser. No. 08/305,823, filed 13 Sep. 1994, now U.S. Pat. No. 5,521,189 which is a continuation-in-part of U.S. patent application Ser. No. 08/238,766, filed 06 May 1994, the disclosures of which are incorporated herein by reference in their entirety.

FIELD OF THE INVENTION

The present invention relates to methods of combatting *Pneumocystis carinii* Pneumonia with dicationic compounds and novel compounds useful therefor. Specifically, the present invention relates to methods of combatting *Pneumocystis carinii* pneumonia with bis-aryl pyrimidine and novel bis-aryl pyrimidines useful therefor.

BACKGROUND OF THE INVENTION

Pentamidine is used for the treatment of *Pneumocystis carinii* pneumonia, or "PCP". The importance off pentamidine has dramatically escalated recently due to the marked increase of patients suffering from PCP. The increase in the afflicted patient population is an unfortunate consequence of the increasing presence of the Acquired Immunodeficiency Syndrome ("AIDS"). It is now estimated that approximately 70 percent of AIDS patients contract PCP. Because of the high incidence of PCP in AIDS patients, pentamidine has found utility not only in the treatment of PCP, but also as prophylaxis, in preventing or delaying the initial onset or recurrence of PCP, especially in AIDS patients. Currently, pentamidine is most commonly administered as a therapeutic agent by intravenous infusion and as a prophylactic agent by aerosol dosage.

However, an unfortunate side effect of pentamidine is its toxicity. Some fatalities have been attributed to severe hypotension, hypoglycemia, and cardiac arrhythmias in patients treated with pentamidine. Contrawise, insufficient dosage may result in dissemination of disease beyond the lung, an occurrence which is associated with a poor prognosis.

Pentamidine is presently in limited use because of cost and toxicity. Therapeutic drug monitoring is not used because of the cost and complexity of the currently available assay techniques which require the extraction of plasma and High Performance Liquid Chromatography analysis. As a result, the toxicity of pentamidine is a significant concern, which is driving the market toward the development of pentamidine substitutes capable of avoiding or minimizing the undesirable side effects associated with the use off pentamidine. Accordingly, it is an object of the present invention to provide new methods of treating *Pneumocystis carinii* pneumonia.

SUMMARY OF THE INVENTION

As a first aspect, the present invention provides a method of treating *Pneumocystis carinii* pneumonia. The method includes administering to a subject in need of such treatment, a compound of Formula I:

wherein:

X and Y are located in the para or meta positions and are selected from the group consisting of H, loweralkyl, loweralkoxy, and wherein:

each $R_1$ is independently selected from the group consisting of H, loweralkyl, alkoxyalkyl, hydroxyalkyl, aminoalkyl, alkylaminoalkyl, cycloalkyl, aryl, or alkylaryl or two $R_1$ groups together represent $C_2$–$C_{10}$ alkyl, hydroxyalkyl, or alkylene, or two $R_1$ groups together represent wherein m is from 1–3 and $R_7$ is H or $CONHR_8NR_9R_{10}$, wherein $R_8$ is loweralkyl, and $R_9$ and $R_{10}$ are each independently selected from the group consisting of H and lower alkyl;

$R_2$ is H, hydroxy, loweralkyl, alkoxyalkyl, hydroxyalkyl, aminoalkyl, alkylaminoalkyl, cycloalkyl, aryl, or alkylaryl;

n is a number from 0 to 2 (where n is 0, the bond is direct covalent linkage between the rings);

$R_3$ and $R_4$ are each independently selected from the group consisting of H, loweralkyl, loweralkoxy, alkylaryl, aryl, oxyaryl, aminoalkyl, aminoaryl, or halogen; and $R_5$ and $R_6$ are each independently selected from the group consisting of H, loweralkyl, aryl, alkylaryl, aminoalkyl, aminoaryl, halogen, oxyalkyl, oxyaryl, or oxyarylalkyl; or a phamaceutically acceptable salt thereof. The compounds of Formula I are administered in an amount effective to treat *Pneumocystis carinii* pneumonia.

As a second aspect, the present invention provides compounds useful for the treatment of *Pneumocystis carinii* pneumonia. The compounds have the structural Formula I, described above. Currently preferred compounds of Formula I include, but are not limited to, 2,4-bis-(4-guanylphenyl)pyrimidine, 2,4-bis-(4-imidazolin-2-yl)pyrimidine, 2,4-bis-[(tetrahydropyrimidinyl-2-yl)phenyl]pyrimidine, 2-(4-[N-i-propylguanyl]phenyl)-4-(2-methoxy-4-[N-i-propylguanyl]phenyl)pyrimidine, and pharmaceutically acceptable salts thereof.

As a third aspect, the present invention provides a method of treating *Giardia lamblia* in a patient in need of such treatment. The method includes administering to a patient in need of such treatment, a compound of Formula I above, in an amount effective to treat *Giardia lamblia*.

As a fourth aspect, the present invention provides a method of treating *Cryptosporidium parvum* in a patient in need of such treatment. The method includes adminstering to a patient in need of such treatment, a compound of Formula I above, in an amount effective to treat *Cryptosporidium parvum*.

The foregoing and other objects and aspects of the present invention are explained in detail in the specification set forth hereinbelow.

DETAILED DESCRIPTION OF THE INVENTION

The term "loweralkyl," as used herein, refers to $C_1$ to $C_4$ linear or branched alkyl, such as methyl, ethyl, propyl, butyl, isopropyl, sec-butyl, and tert-butyl. Methyl, ethyl, and isopropyl are currently preferred. The term loweralkoxy as used herein, refers to $C_1$ to $C_4$ linear or branched alkoxy, such as methoxy, ethoxy, propyloxy, butyloxy, isopropyloxy, and t-butyloxy. Methoxy is currently preferred.

As noted above, the methods of the present invention are useful for treating *Pneumocystis carinii* pneumonia and *Giardia lamblia*. The methods of the present invention are useful for treating these conditions in that they inhibit the onset, growth, or spread of the condition, cause regression of the condition, cure the condition, or otherwise improve the general well-being of a subject inflicted with, or at risk of contracting the condition.

Subjects to be treated by the methods of the present invention are typically human subjects although the methods of the present invention may be useful with any suitable subject known to those skilled in the art.

As noted above, the present invention provides pharmaceutical formulations comprising the aforementioned compounds of Formula I, or pharmaceutically acceptable salts thereof, in pharmaceutically acceptable carriers for aerosol, oral, and parenteral administration as discussed in greater detail below. Also, the present invention provides such new compounds or salts thereof which have been lyophilized and which may be reconstituted to form pharmaceutically acceptable formulations for administration, as by intravenous or intramuscular injection.

Obviously, the therapeutically effective dosage of any specific compound, the use of which is in the scope of present invention, will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration. The duration of the treatment is usually once per day for a period of two to three weeks or until the *Pneumocystis carinii* pneumonia is essentially controlled. Lower doses given less frequently can be used to prevent or reduce the incidence of recurrence of the infection.

In accordance with the present method, a compound of Formula I, or a pharmaceutically acceptable salt thereof, may be administered orally or through inhalation as a solid, or may be administered intramuscularly or intravenously as a solution, suspension, or emulsion. Alternatively, the compound or salt may also be administered by inhalation, intravenously or intramuscularly as a liposomal suspension. When administered through inhalation the compound or salt should be in the form of a plurality of solid particles or droplets having a particle size from about 0.5 to about 5 microns, preferably from about 1 to about 2 microns.

Besides providing a method for treating *Pneumocystis carinii* pneumonia, the compounds of Formula I also provide a method for prophylaxis against *Pneumocystis carinii* pneumonia in an immunocompromised patient, such as one suffering from AIDS, who has had at least one episode of *Pneumocystis carinii* pneumonia, but who at the time of treatment is not exhibiting signs of pneumonia. As *Pneumocystis carinii* pneumonia is an especially potentially devastating disease for immunocompromised patients it is preferable to avoid the onset of *Pneumocystis carinii* pneumonia, as compared to treating the disease after it has become symptomatic. Accordingly, the present invention provides a method for the prophylaxis against *Pneumocystis carinii* pneumonia comprising administering to the patient a prophylactically effective amount of a compound of Formula I or a pharmaceutically acceptable salt thereof. The forms for administration of the compound or salt in accordance with this method may be the same as utilized for the purpose of actually treating a patient suffering from *Pneumocystis carinii* pneumonia.

An additional useful aspect of the present invention is a method for prophylaxis against even an initial episode of *Pneumocystis carinii* pneumonia in an immunocompromised patient who has never experienced an episode of *Pneumocystis carinii* pneumonia. In this respect, a patient who has been diagnosed as being immunocompromised, such as one suffering from AIDS or ARC (AIDS related complex), even before the onset of an initial episode of *Pneumocystis carinii* pneumonia, may avoid or delay suffering from the infection by having administered a prophylactically effective amount of a compound of Formula I or a pharmaceutically acceptable salt thereof. The compound or salt may be administered in the same fashion as in the treatment of patients suffering from *Pneumocystis carinii* pneumonia.

The present invention also provides new pharmaceutical compositions suitable for intravenous or intramuscular injection. The pharmaceutical compositions comprise a compound of Formula I, or a pharmaceutically acceptable salt thereof, in any pharmaceutically acceptable carrier. If a solution is desired, water is the carrier of choice with respect to water-soluble compounds or salts. With respect to the water-insoluble compounds or salts, an organic vehicle, such as glycerol, propylene glycol, polyethylene glycol, or mixtures thereof, may be suitable. In the latter instance, the organic vehicle may contain a substantial amount of water. The solution in either instance may then be sterilized in any suitable manner, preferably by filtration through a 0.22 micron filter. Subsequent to sterilization, the solution may be filled into appropriate receptacles, such as depyrogenated glass vials. Of course, the filling should be done by an aseptic method. Sterilized closures may then be placed on the vials and, if desired, the vial contents may be lyophilized.

In addition to compounds of Formula I or their salts, the pharmaceutical compositions may contain other additives, such as pH adjusting additives. In particular, useful pH adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In yet another aspect of the present invention, there is provided an injectable, stable, sterile composition comprising a compound of Formula I, or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into man. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Other pharmaceutical compositions may be prepared from the water-insoluble compounds of Formula I, or salts thereof, such as aqueous base emulsions. In such an instance, the composition will contain a sufficient amount of pharmaceutically acceptable emulsifying agent to emulsify the desired amount of the compound of Formula I or salt thereof. Particularly useful emulsifying agents include phosphatidyl cholines, and lecithin.

Further, the present invention provides liposomal formulations of the compounds of Formula I and salts thereof. The technology for forming liposomal suspensions is well known in the art. When the compound of Formula I or salt thereof is an aqueous-soluble salt, useing conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds of Formula I or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of the desired compound of Formula I or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the solid compound of Formula I, or a salt thereof, in any appropriate manner known in the art, such as by micronization. Most preferably, the size of the solid particles or droplets will be from about 1 to about 2 microns. In this respect, commercial nebulizers are available to achieve this purpose.

Preferably, when the pharmaceutical formulation suitable for administration as an aerosol is in the form of a liquid, the formulation will comprise a water-soluble compound of Formula I or a salt thereof, in a carrier which comprises water. A surfactant may be present which lowers the surface tension of the formulation sufficiently to result in the formation of droplets within the desired size range when subjected to nebulization.

As indicated, the present invention provides both water-soluble and water-insoluble compounds and salts. As used in the present specification, the term "water-soluble" is meant to define any composition which is soluble in water in an amount of about 50 mg/mL, or greater. Also, as used in the present specification, the term "water-insoluble" is meant to define any composition which has solubility in water of less than about 20 mg/mL. For certain applications, water soluble compounds or salts may be desirable whereas for other applications water-insoluble compounds or salts likewise may be desirable.

Examples of compounds exemplary of Formula (I) above include, but are not limited to:

(1) 2,4-bis-(4-guanylphenyl)-pyrimidine, (2) 2,4-bis-(4-imidazolin-2-yl)-pyrimidine, (3) 2,4-bis-[(tetrahydropyrimidinyl-2-yl)phenyl]pyrimidine, (4) 2-(4-[N-i-propylguanyl]phenyl)-4-(2-methoxy-4-[N-i-propylguanyl]phenyl)pyrimidine.

Compounds employed in carrying out the present invention may be prepared in accordance with techniques known to those skilled in the art (see, e.g., U.S. Pat. No. 4,933,347), particularly in light of the disclosure and examples set forth below.

As indicated, the compounds used in the present invention may be present as pharmaceutically acceptable salts. Such salts include the gluconate, lactate, acetate, tartarate, citrate, phosphate, borate, nitrate, sulfate, and hydrochloride salts.

The salts of the present invention may be prepared, in general, by reacting two equivalents of the pyrimidine base compound with the desired acid, solution. After the reaction is complete, the salts are crystallized from solution by the addition of an appropriate amount of solvent in which the salt insoluble.

Methods of combating *Giardia lamblia* with the compounds of Formula I above are carried out in essentially the same manner as given above, and pharmaceutical formulations of the compounds of Formula I for combating *Giardia lamblia* are prepared in essentially the same manner as given above.

Methods of combating *Cryptosporidium parvum* with the compounds of Formula I above are carried out in essentially the same manner as given above, and pharmaceutical formulations of the compounds of Formula I for combating *Cryptosporidium parvum* are prepared in essentially the same manner as given above.

The compounds of the present invention are useful not only in methods for treating *Pneumocystis carinii* pneumonia, *Giardia lamblia*, and *Cryptosporidium parvum*, but also in methods of inihibiting enzymes such as topoisomerase.

The compounds of Formula I are particularly useful for inhibiting topoisomerase II. See, S. Doucc-Racy, et al., *Proc. Natl. Acad. Sci.* USA 83:7152 (1986).

As noted above, the compounds of the present invention may be prepared according to methods known in the art. For example, compounds of Formula I above may be prepared by first preparing an appropriate intermediate, such as 2,4-bis(4-bromophenyl)pyrimidine. The intermediate is prepared by the base promoted condensation of 4-bromobenzamidine and 1-dimethylamino-3-dimethylimmonio-1-(4-bromophenyl)-1-propene, according to the method of R. Wagner, et al., *Chem. Ber.* 104: 2975 (1971). The bis-nitrile is readily obtainable by reacting copper(I) cyanide with the thus prepared intermediate in refluxing DMF according to the standard techniques. See, J. Spychala, et al., *European J. Med. Chem.* 29:363 (1994). The bis-nitrile is converted to the imidate ester by the Pinner methodology, according to B. Das, et al., *J. Med. Chem.* 20:1219 (1977). The compounds of Formula I are obtained from the imidate ester according to known techniques. See, Das, et al., supra. Scheme 1 below, outlines the foregoing procedure for preparing compounds of Formula I.

"MS" means mass spectroscopy, "Hz" means hertz, "g" means grams, "mL" means milliliters, "L" means liters, "hr" means hours, "C" means degrees Centigrade, "DMSO" means dimethyl sulfoxide, "DMF" means dimethyl formamide, and "m/e" means mass divided by charge. These Examples are illustrative and are not to be taken as limiting of the invention.

EXAMPLE 1

Preparation of 1-Dimethylamino-3-dimethylimonio-1-(4-bromophenyl)-1-propene perchlorate Using the method of A. Holy, et al., *Collect. Czech. Chem. Comm.* 30:4127 (1965), freshly distilled phosphorus oxychloride (122.8 g, 0.8 mole) is added, dropwise, to a cooled and stirred solution of 73 g (1.0 mole) dry dimethylformamide in 150 mL dry chloroform. The solution turns reddish-pink during addition and is stirred for 1 hr. 4-Bromoacetophenone (39.8 g, 0.2 mole) in 100 mL of dry chloroform is added to the previously prepared solution and the mixture is heated to 50°–60° C. for 3 hr. After the mixture is allowed to cool it is poured into stirred ice cold water (external cooling required). The aqueous solution is extracted with 100 mL ether, after which aqueous dimethylamine (40% solution) is added slowly, with cooling, to the aqueous layer. The resulting thick yellow precipitate is filtered and is

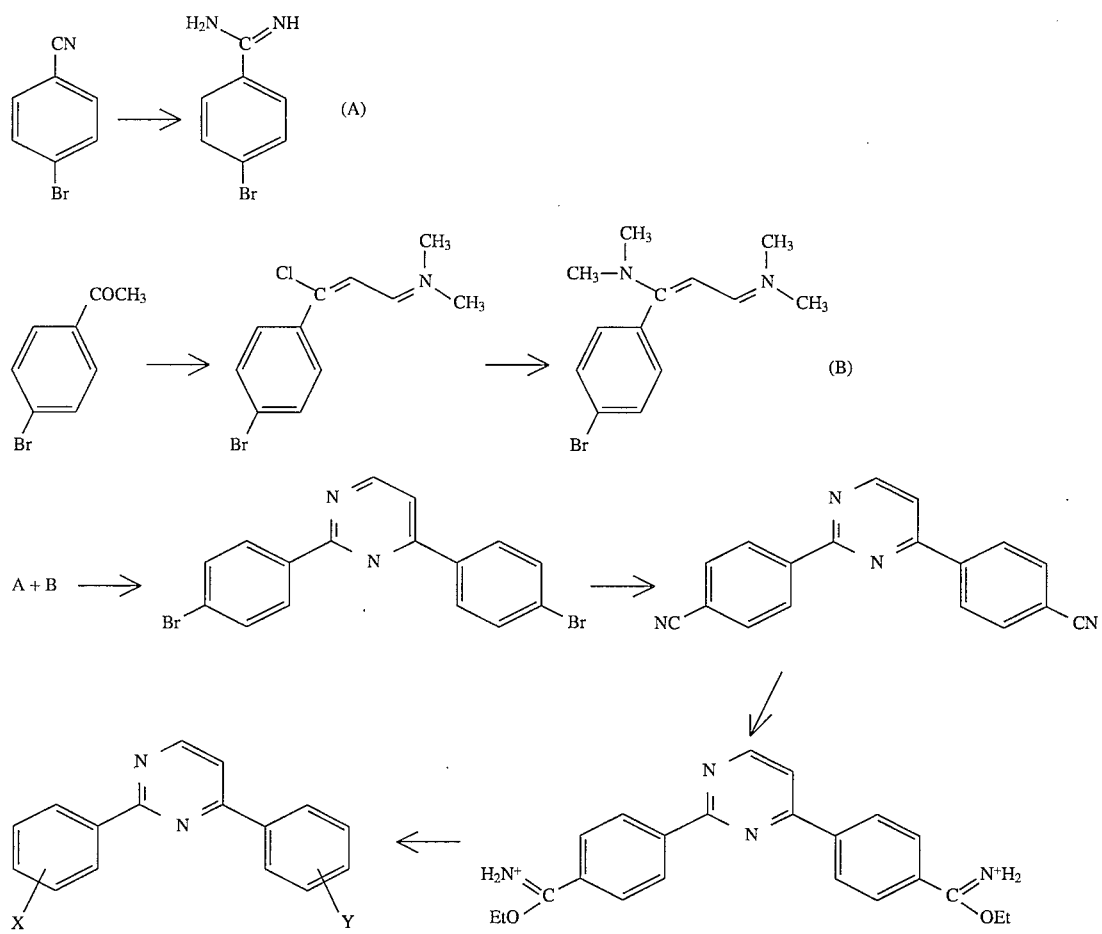

The present invention is explained in greater detail in the following examples. As used herein, "mp" means melting point, "NMR" means nuclear magnetic resonance, "MHz" means megahertz, "FAB" means fast atomic bombardment, "EI" means electon ionization, "IR" means infrared spectra, resuspended in 200 mL of water. A solution of sodium perchlorate (34 g, 0.28 mole) in 50 mL water is added to the suspension, and a thick yellow precipitate is obtained. The precipitate is filtered and dried in vacuo at 50° C. for 12 hr. The yellow solid is dissolved in 400 mL of boiling absolute ethanol. After cooling, the off-white crystalline precipitate is filtered, washed with dry ether and dried in vacuo at 50° C. for 24 hr. Yield=50.5 g (66%).

Characterization: mp=160°–62° C. IR(KBr): 2391, 1630, 1561, 1394, 836 cm$^{-1}$. $^1$H-NMR (DMSO-d$_6$): 7.76 (d, 2H, j=8 Hz), 7.27 (d, 2H, j=8 Hz), 6.91 (d, 1H, j=12 Hz), 3.31 (s, 3H), 3.13 (s, 3H), 3.11 (s, 3H), 2.87 (s, 3H). $^{13}$C-NMR (DMSO-d$_6$): 169.4, 160.9. 131.0, 130.8, 130.5, 123.9, 91.8, 45.8, 42.8, 40.8, 38.1. MS m/e: 281 (M$^+$ -HClO$_4$).

EXAMPLE 2

Preparation of 4-Bromobenzamidine benzenesulfonate

A stirred mixture of 4-bromobenzonitrile (36.4 g, 0.2 mole) and ammonium benzenesulfonate (45 g, 0.26 mole) is gradually heated to 260°–279° C. (bath temp.) for 2.5 hr; at this temperature the melt becomes a clear liquid (both boiling and sublimation of the mixture is observed). The bath is removed and the melt is slowly and carefully added to 600 mL of acetone to dissolve any unreacted nitrile and also to prevent the melt from becoming a hard solid mass. Any lumps remaining are broken and the solid is filtered. The solid is thoroughly ground and then slurried with water to remove any excess ammonium benzene sulfonate and filtered. The solid is again slurried with acetone and filtered, washed with dry ether and dried in vacuo at 100° C. for 12 hr. Yield: 33 g (51% based on recovered nitrile). The acetone extract yielded unreacted p-bromobenzonitrile (12.8 g).

Characterization: mp 253° C. (literature value: 250°–260° C.). IR(KBr): 3325, 3126, 1681, 1597 cm$^{-1}$. $^1$H-NMR (DMSO-d$_6$): 9.15 (s, 4H), 7.8 (q, 4H), 7.32 (m, 2H), 7.23 (m, 3H). $^{13}$C-NMR (DMSO-d$_6$): 164.8, 147.8, 131.9, 130.0, 128.4, 127.5, 127.2, 125.3.

EXAMPLE 3

Preparation of 4-Bromobenzamidine

Sodium hydroxide (6–7 mL of 5M) is added to a stirred mixture of the amidine salt (3.57 g, 0.01 mole) (produced as in Example 2) in 10 mL of water. Stirring is maintained for 10 min. The solid is filtered, washed with water, and dissolved in 50 mL of acetone. Thereafter, the dissolved solid is treated with charcoal, filtered, and the acetone removed under reduced pressure. The resulting white crystalline solid is washed with dry ether and dried in vacuo at 40° C. for 12 hr. Yield: 1.5 g (75%).

Characterization: mp=168°–169° C. (literature value= 159° C.). IR (KBr): 3420, 3326, 3240, 3050, 1649 cm$^{-1}$. $^1$H-NMR (DMSO-d$_6$, 45° C.): 7.74 (d, 2H, j=8.2 Hz), 7.62 (d, 2H, J=8.2 Hz) 6.43 (br, 3H). $^{13}$C-NMR (DMSO-d$_6$, 45° C.) 161.3, 135.4, 130.7, 128.5, 123.0. MS m/e: 198 (M$^+$).

EXAMPLE 4

Preparation of 2,4-Bis(4-bromophenyl)-pyrimidine

Sodium ethoxide (0.055 mole), prepared from 1.26 g sodium and 70 mL ethanol, is added to a stirred mixture of p-bromobenzamidine benzene sulfonate (10.7 g, 0.03 mole) and 1-dimethylamino-3-dimethylimonio-1-(4-bromophenyl)-1-propene perchlorate (8.4 g, 0.022 mole) in 100 mL of absolute ethanol. After stirring for 30 min at room temperature a further equivalent of sodium ethoxide is added and the mixture is heated under reflux with efficient stirring for 3 hr. The solvent is removed under reduced pressure, and the yellow residue is triturated with 100 mL water. The resulting solid is filtered and washed with water. The yellow cake, after drying, is recrystallized from ether:hexane (2:3) to give colorless needles. Yield: 3.65 g (86%).

Characterization: mp=165°–166° C. IR (KBr): 1585, 1578, 1555, 816, 765 cm$^{-1}$. $^1$H-NMR (CDCl$_3$, 35° C.): 8.71 (d, 1H, j=5.5 Hz), 8.39( d, 2H, j=8.5 Hz), 8.25 (d, 2H, j=8.5 Hz), 7.63 (d, 2H, j=6.7 Hz), 7.6 (d, 2H, j=6.7 Hz), 7.5 (d, 1H, j=5.5 Hz). $^{13}$C-NMR (CDCl$_3$, 35° C.): 163.9, 162.8, 158.0, 136.7, 135.7, 132.2, 131.7, 129.9, 128.6, 125.6, 114.3. MS m/e: 390 (M$^+$).

EXAMPLE 5

2,4-Bis(4-cyanophenyl)-pyrimidine

A mixture of 2,4-bis(4-bromophenyl) pyrimidine (7.8 g, 0.02 mole) and copper (I) cyanide (4.45 g, 0.05 mol) in 50 mL dry dimethylformamide is heated under reflux for 30–35 hr, during which time the color of the mixture changes to dark brown. When the mixture is poured into 300 mL ice cold water, a brown solid precipitated. The mixture is stirred for 3 hr with 300 mL 10% NaCN solution. The solid is filtered, washed with water (1.5 L) and dried. The brown solid cake is placed in a soxlate device and extracted with boiling acetone for 36 hr. The solvent is removed and the light brown solid is chromatographed over neutral Al$_2$O$_3$. Elution with acetone:hexane (7:3) (20×50 mL fractions) and evaporation of the solvent yields pale yellow fluffy needles which are dried in vacuo at 100° C. for 6–7 hr. Yield: 2.7 g (48%).

Characterization: mp 239°–242° C. Elemental analysis calculated for C$_{18}$H$_{10}$N$_4$: C: 76.56, H: 3.57, N: 19.84; found: C: 76.50, H, 3.64, N: 19.75. IR (KBr): 2223, 1580, 1550, 831, 798 cm$^{-1}$. $^1$H-NMR (DMSO-d$_6$, 35° C.:) 9.08 (d, 1H, j=5.4 Hz), 8.65 (d, 2H, j=8.8 Hz), 8.5 (d, 2H, j=8.3 Hz), 8.15 (d, 2H, j=5.4 Hz), 8.03 (d, 2H, j=8.8 Hz), 8.01 (d, 2H, j=8.3 Hz). $^{13}$C-NMR (DMSO-d$_6$, 35° C.): 161.7, 161.2, 159.0, 140.8, 139.8, 139.6, 132.3, 128.2, 127.7, 118.2, 118.0, 116.3, 113.4, 113.1. MS m/e: 282 (M$^+$).

EXAMPLE 6

Preparation of 2,4-Bis-(4-guanylphenyl)pyrimidine hydrochloride

The bis-nitrile of Example 5 (2.8 g, 0.011 mole) is suspended in 250 mL absolute ethanol and cooled in an ice-salt bath. After dry HCl gas is passed through it the compound is dissolved. The clear yellow solution is placed in a pressure bottle and left for 12 hr with occasional shaking. The imidate ester hydrochloride is filtered, washed with dry ether and dried in vacuo to yield 4.2 g. The dried imidate ester is shown to be free of contamination by the bis-nitrile starting material by its IR spectrum.

Dry ammonia is passed through a cold suspension of 2.1 g (0.0043 mole) of the imidate ester in 50 mL absolute ethanol until saturated. The mixture is shaken for 2 days after which the solvent is removed, the resulting solid suspended in water, and made basic to a pH greater than 9 with 10% NaHCO$_3$. The free base which precipitates is filtered and dried in vacuo at 70° C. for 12 hr. The off-white solid is recrystallized from boiling ethanol. Yield: 1.1 g (69%).

Characterization: mp=237°–39° C. Elemental analysis calculated for $C_{18}H_{16}N_6 \cdot 0.5H_2O$: C: 66.42, H: 5.06, N: 25.82; found: C: 66.46, H: 5.04, N: 25.82. IR (KBr): 3459, 3349, 3251, 1649, 1584 cm$^{-1}$. $^1$H-NMR (CD$_3$CO$_2$D, 70° C.): 9.05 (d, 1H, j=5.4 Hz), 8.71 (d, 2H, j=8.8 Hz), 8.49 (d, 2H, j=8.8 Hz), 8.08 (d, 2H, 8.8 Hz). $^{13}$C-NMR (CD$_3$CO$_2$D, 70° C.): 167.5, 167.3, 164.2, 163.8, 160.0, 143.7, 142.8, 131.4, 131.0, 130.1, 129.7, 129.3, 129.2, 117.5. MS m/e: 316 (M$^+$). FAB m/e: 317 (M$^+$+H).

The bis-guanyl compound (0.8 g, 0.0025 mole) is suspended in 25 mL absolute ethanol, to which 25 mL saturated ethanolic HCl is added and the mixture refluxed for 1 hr. After cooling, the volume is reduced to 15 mL. The resulting off-white solid is filtered and washed with dry ether. The salt is dried in vacuo at 80° C. for 24 hr. Yield: 1.0 g (94%).

Characterization: mp>36° C. (sublimes). Elemental analysis calculated for $C_{18}H_{16}N_6 \cdot 3$ HCl: C: 50.78, H: 4.49, N: 19.74; found: C: 50.85, H: 4.53, N: 19.68. IR (KBr): 3356, 3249, 3007, 1684, 1609 cm$^{-1}$. $^1$H-NMR (D$_2$O/TSP/ 50° C.): 8.43 (d, 1H, j=5.4 Hz), 7.87 (d, 2H, j=7.8 Hz), 7.81 (d, 2H, j=7.8 Hz), 7.57 (d, 4H, j=7.8 Hz), 7.44 (d, 1H, j=5 Hz). $^{13}$C-NMR (D$_2$O/TSP/50° C.): 162.3, 162.2, 158.9, 158.3, 155.0, 137.8, 137.0, 126.5, 126.1, 125.7, 125.3, 125.1, 125.0, 113.4. MS FAB m/e: 317 (M+ +H).

EXAMPLE 7

Preparation of 2,4-Bis-[(4-imidazolin-2-yl)phenyl]-pyrimidine hydrochloride]

After suspending the bis-imidate ester hydrochloride of Example 6 (2.1 g, 0.0043 mole) in 50 mL absolute ethanol, ethylene diamine 0.06 g, 0.01 mole) is added and the mixture is refluxed for 12 hr. The solvent is evaporated and the resulting solid is triturated with water. The off-white solid thus obtained is filtered, washed with water and dried. The free base is boiled with 800 mL of absolute ethanol and filtered to yield a beige crystalline solid. Yield: 1.3 g (94%).

Characterization: mp 337°–339° C. (dec.) (turns brown at 320° C. and black at mp). Elemental analysis calculated for $C_{22}H_{20}N_6$: C: 71.72, H: 5.47, N: 22.80; found: C: 71.70, H: 5.48, N: 22.75. IR (KBr): 3190.2, 1615.4, 1602.6, 1575.8 cm$^{-1}$. $^1$H-NMR (CD$_3$CO$_2$D) 65° C.: 9.04 (d, 1H, j=5.4 Hz), 8.72 (d, 2H, j=8.3 Hz), 8.49 (d, 2H, j=8.8 Hz), 8.16 (d, 2H, j=8.3 Hz), 8.1 (d, 2H, j=8.8 Hz), 7.98 (d, 1H, j=5.4 Hz), 4.19 (s, 8H). $^{13}$C-NMR (CD$_3$CO$_2$D) 65° C.: 167.02, 166.8, 163.9, 163.6, 144.1, 143.0, 139.4, 130.1, 130.0, 129.2, 125.5, 125.1, 117.6, 46.1. MS EI: 368.2 (M$^+$).

The free base (1.0 g, 0.0027 mole) is suspended in 35 mL saturated ethanolic HCl and refluxed for 1 hr (not all the solid is dissolved). The solvent is reduced under pressure to a volume of 5–6 mL, diluted with dry ether and filtered, washed with dry ether and dried in vacuo at 100° C. for 24 hr. Yield: 1.2 g.

Characterization: mp>360° C. (does not melt; turns brown at ca. 345° C.). Elemental analysis calculated for $C_{22}H_{20}N_6 \cdot 3$ HCl: C: 52.33, H: 5.19, N: 16.64; found: C 52.51, H: 5.20, N: 16.60. IR (KBr): 3405, 3060, 2945, 1618, 1607, 1572. $^1$H-NMR (D$_2$O/Dioxane/45° C.): 8.73 (d, 1H, j=5.5 Hz), 8.13 (d, 2H, j=7.9 Hz), 8.03 (d, 2H, j=7.9 Hz), 7.71 (m, 5H), 4.02 (s, 4H), 4.01 (s, 4H). $^{13}$C-NMR (D$_2$O/ Dioxane/45° C.): 164.7, 164.5, 161.2, 158.3, 141.2, 140.2, 128.4, 128.2, 127.7, 123.6, 123.3, 116.2, 44.5. MS EI m/e: 368.2 (M$^+$).

EXAMPLE 8

Preparation of 2,4-Bis-[(4-tetrahydropyrimidinyl-2-yl)phenyl)-pyrimidine hydrochloride]

The bis-imidate ester hydrochloride produced in Example 7 (2.1 g, 0.0043 mole) is suspended in 50 mL anhydrous ethanol. Fresh distilled 1,3-diaminopropane (0.74 g, 0.01 mole) is added and a clear pale yellow solution is formed. The mixture is refluxed for 12 hr. The solvent is removed under reduced pressure and the solid is suspended in water and made basic, while cooling, with diluted NaOH to pH=10. The off-white solid thus obtained is filtered, washed with water and crystallized from an ethanol:ether mixture to yield 0.91 g (53%).

Characterization: mp=165°–66° C. IR (KBr): 3350, 3179, 3035, 2945, 1633, 1575, 1438, 1367, 1197, 832, 696 cm$^{-1}$. $^1$H-NMR (DMSO-d$_6$, 35° C.): 8.96 (d, 1H, j=5.4 Hz), 8.52 (d, 2H, j=8.3 Hz), 8.04 (d, 2H, j=5.4 Hz), 7.95 (d, 2H, j=8.3 Hz) 3.41-3.37 (m, 8H), 1.73-1.72 (m, 4H). $^{13}$C-NMR (DMSO-d$_6$, 35° C.) 162.9, 162.4, 158.6, 153.1, 152.7, 138.8, 138.2, 138.1, 136.8, 127.7, 126.4, 115.3, 41.4, 41.3, 20.4, 20.3. MS m/e: 396 (M$^+$).

The free base (0.6 g, 0.0015 mole) is heated in a 10 mL saturated ethanolic HCl solution for 2 hr, concentrated to 2 mL, and triturated with dry ether. The precipitated solid is filtered, washed with ether, and dried in vacuo at 65° C. for 24 hr to yield 0.63 g (82%).

Characterization: m.p 267°–68° C. Elemental analysis calculated for $C_{24}H_{24}N_6 \cdot 3$ HCl: C: 55.97, H: 5.48, N: 16.32; found: C: 55.90, H: 5.52, N: 16.27. IR (KBr): 3425, 3179, 3025, 1640, 1620, 1574, 1400, 1013, 832, 693 cm$^{-1}$. $^1$H-NMR (CD$_3$SOCD$_3$/45° C.): 10.5 (s, 2H), 10.43 (s, 2H), 9.08 (d, 1H, j=5.4 Hz), 8.68 (d, 3H, j=8.3 Hz), 8.55 (d, 2H, j=8.3 Hz), 8.21 (d, 1H, j=5.4 Hz), 8.08 (d, 2H, j=8.4 Hz), 8.03 (d, 2H, j=8.8 Hz), 3.52 (m, 6H), 2.0 (m, 4H). $^{13}$C-NMR: (CD$_3$SOCD$_3$/40° C.):162.2, 161.7, 159.2, 158.5, 158.3, 141.0, 139.9, 130.5, 130.3, 128.5.128.2, 128.0, 127.4, 116.44, 38.9, 17.6.

EXAMPLE 9

Preparation of 2-phenyl-4-(4-bromophenyl)-pyrimidine

Benzamidine hydrochloride (4.7 g, 0.03 mole) and 1-dimethylamino-3-dimethylimonio-1-(4-bromophenyl)-1-propene perchlorate are allowed to react as described above in Example 4 for the preparation of 2,4-Bis(4-bromophenyl)-pyrimidine. After work-up and recrystallization from CHCl$_3$:ethyl ether (1:3), 7.2 g (72%) of a white crystalline solid is obtained which melted at 107°–08° C. IR(KBr) 2925, 1597, 1562, 1540, 1427 cm$^{-1}$. $^1$H-NMR: (CDCl$_3$) 8.65 (d, 1H, j=5.3 Hz), 8.55-8.52 (m, 2H), 8.02 (d, 2H, j=8.3 Hz), 7.6 (d, 2H, j=8.8 Hz), 7.5-7.46 (m, 3H), 7.44 (d, 1H, j=5.3 Hz). $^{13}$C-NMR (CDCl$_3$): 164.6, 162.5, 157.9, 137.6, 135.7, 132.1, 130.8, 128.6, 128.5, 128.2, 125.6, 114.1. MS m/e: 311 (M$^+$).

EXAMPLE 10

Preparation of 2-phenyl-4-(4-cyanophenyl)-pyrimidine

2-Phenyl-4-(4-bromophenyl)-pyrimidine (6.2 g, 0.03 mole), copper (I) cyanide (2.7 g, 0.03 mole) and 30 mL of DMF are allowed to reflux for 30 hr. After working-up the mixture as described in Example 5, and recrystallization from ethyl ether: CHCl₃ (3:1) a white crystalline solid is obtained. Yield: 2.3 g (55%).

Characterization: mp 125°–126° C. IR (KBr): 2235, 2277, 1592, 1562, 1425 cm$^{-1}$. $^1$H-NMR (DMSO-d$_6$/90° C.): 9.0 (d, 1H, j=5.3 Hz), 8.5-8.45 (m, 2H), 8.4 (d, 2H, j=8.3 Hz), 8.04 (d, 1H, j=5.3 Hz), 8.01 (d, 2H, j=8.8 Hz), 7.55-7.53 (m, 3H). $^{13}$C-NMR (DMSO-d$_6$/90° C.): 163.4, 161.0, 159.0, 140.0, 136.9, 132.8, 130.9, 127.8, 118.3, 115.7, 113.3. MS m/e: 257 (M⁺).

EXAMPLE 11

Preparation of 2-phenyl-4-(4-imidazolin-2-yl)-phenylpyrimidine hydrochloride A solution of 2-phenyl-4(-cyanophenyl)-pyrimidine (1.35 g, 0.0005 mole) in dry ethanol is saturated with anhydrous HCl, and the mixture is stirred for 3 days at room temperature. The resulting imidate ester hydrochloride is isolated and dried in vacuo as described above in Example 6. The imidate is allowed to react with ethylene diamine as described above in Example 7, and yields 0.8 g (70%) of white solid which melts at 200°–02° C. after recrystallization from ethanol.

Characterization: IR (KBr): 3176, 2925, 2865, 1606, 1562, 1422 cm$^{-1}$. $^1$H-NMR (CDCl₃/40° C.): 8.84 (d, 1H, j=5.5 Hz), 8.8-8.55 (m, 2H), 8.25 (d, 2H, j=8.6 Hz), 7.95 (d, 2H, j=8.6 Hz), 7.6 (d, 1H, j=5.5 Hz), 3.83 (s, 4H). $^{13}$C-NMR (CDCl₃/50° C.): 163.3, 162.9, 162.1, 158.5, 139.7, 137.1, 132.9, 130.6, 128.4, 127.7, 127.5, 126.7, 115.0, 49.5. MS m/e: 299 (M⁺).

The free base is converted into the hydrochloride salt by standard procedures to yield a white solid (85%). Characterization: mp>300° C. IR (KBr): 3033, 2876, 2710, 1607, 1587 cm$^{-1}$. $^1$H-NMR (DMSO-d$_6$/50° C.): 1125 (s, 2H), 8.95 (d, 1H, j=5.5 Hz), 8.54-8.44 (m, 2H), 8.52 (d, 2H, j=8.6 Hz), 8.37 (d, 2H, j=8.6), 8.15 (d, 1H, j=5.5 Hz) 7.75 (s, 1HNH) 7.55-7.53 (m, 3H), 4.02 (s, 4H). $^{13}$C NMR (DMSO-d$_6$/50° C.): 163.9, 163.3, 161.1, 158.7, 141.2, 136.8, 130.7, 129.4, 127.3, 124.0, 115.6, 44.2. Elemental analysis calculated for C₁₉H₁₅N₄·2HCLO·5H₂O: C: 59.85, H: 4.75, N: 14.69; found: C: 60.02, H: 4.83, N: 14.94.

EXAMPLE 12

Biological Evaluation

TABLE 1

| Compound | DNA binding[a] | Topoisomerase G. lamblia[b] | Topoisomerase P. Carinii[c] | G. lamblia IC$_{50}$[d] |
|---|---|---|---|---|
| Pentamidine | 12.8 | — | >100 | 2.6 |
| Saline | — | — | — | — |
| 1 | 21.5 | >100 | 20 | 2.0 |
| 2 | 22.7 | 50 | 30 | 3.0 |
| 3 | 25 | >100 | 20 | 0.79 |
| 4 | 0.6 | 100 | — | 2.0 |
| 5 | 13.9 | 200 | no | 36.7 |

Compounds:
1: 2,4-Bis(4-guanyl)-pyrimidine hydrochloride
2: 2,4-Bis[(4-imidazolin-2-yl)phenyl]pyrimidine hydrochloride
3: 2,4-Bis[(4-tetrahydropyrimmidinyl-2-yl)phenyl]pyrimidine hydrochloride
4: 2-phenyl-4-[4-(imidazolin-2-yl)phenyl]pyrimidine hydrochloride
5: 2-(4-[N-i-propylguanyl]phenyl)-4-(2-methoxy-4-[N-i-propylguanyl]phenyl)pyrimidine TABLE 1-continued

| Compound | DNA binding[a] | Topoisomerase G. lamblia[b] | Topoisomerase P. Carinii[c] | G. lamblia IC$_{50}$[d] |
|---|---|---|---|---|

[a]Increase in thermal melting of poly dA.dT. See, W. Wilson, et al., Biochemistry 32:4098 (1993).
[b]Inhibition of topoisomerase II isolated from *G. lamblia*. Correlation of topoisomerase II inhibition with anti-*Giardia lamblia* activity. See, C. Bell, et al., Antimicrob. Agents Chemother. 37:2668 (1993).
[c]Inhibition of topoisomerase II isolated from *P. carinii*. See, C. Dykstra, et al., J. Protozool. 38:78S (1991).
[d]50% Inhibitory concentration against *G. lamblia, P. carinii* topoisomerase. See, Bell, et al., supra.

TABLE 2

In vivo Activity Against *Pneumocystis carinii* in Rats

| Compound | mg/Kg per day | Toxicity | cyst/g Lung |
|---|---|---|---|
| Pentamidine | 10.0 | 2+ | — |
| Saline | — | 0 | 100% |
| 1 | 10.0 | 1+ | 0.8% |
| 1 | 5.0 | 0 | 2.4% |
| 2 | 5.0 | 0 | 2.4% |
| 3 | 2.5 | +++ | 85.2% |
| 4 | 5.0 | + | 21.1% |
| 5 | 2.5 | — | 1.0% |

Compounds:
1: 2,4-Bis(4-guanyl)pyrimidine hydrochloride
2: 2,4-Bis[(4-imidazolin-2-yl)phenyl]pyrimidine hydrochloride
3: 2,4-Bis[(4-tetrahydropyrimmidinyl-2-yl)phenyl]pyrimidine hydrochloride
4: 2-phenyl-4-[4-(imidazolin-2-yl)phenyl]pyrimidine hydrochloride
5: 2-(4-[N-i-propylguanyl]phenyl)-4-(2-methoxy-4-[N-i-propylguanyl]phenyl)pyrimidine

TABLE 3

Inhibition of *C. Parvum*

| Compound | mg/kg/day | % efficacy |
|---|---|---|
| 1 | 25 | 50 |
| 1 | 5 | 68 |
| 1 | 0.1 | 30 |

1: 2,4-Bis(4-guanyl)-pyrimidine hydrochloride

EXAMPLE 13

2-(4-Bromophenyl)-4-(2-methoxy-4-bromophenyl)pyrimidine

To a stirred suspension of 3-dimethylamino-1-(4-bromophenyl) propenone (14.1 g, 0.05 mole) and 4-bromobenzamidine benzenesulfonate (17.2 g, o.51 mole) in 75 mL absolute ethonal is added sodium ethoxide ( 0.1 mole, from 2.3 g Na) in 70 mL absolute ethanol. The mixture is heated at reflux for 24 hr (TLC monitored) and the solvent distilled. The residue is triturated with 100 mL of water, and the remaining solid precipitate is filtered, washed with water, dried and redissolved in 200 mL chloroform dried over Na₂SO₄ (anhydrous). The excess solvent is distilled and the residue is crystallized from CHCl₃: ether (1:4), to yield 13.2 g of an off-white crystalline solid (62%) having amp of 153°–5° C.

Characterization: IR(KBr) 3040, 2920, 1592, 1560, 1433, 1387, 1235, 1039, 859, 807 cm$^{-8}$. $^1$H NMR (CDCl₃), 8.74 (d, 1H, j=8.8), 8.10 (d, 1H, j=8.3), 7.83 (d, 1H, j=5.4), 7.61 (d, 2H, j=8.3), 7.28 (d, 1H, j=1.95), 7.17 (s, 1H), 3.91 (s, 3H). $_{13}$C NMR (CDCl³) 163.4, 161.6, 158.6, 157.1, 136.9, 132.3, 131.7, 129.7, 125.7, 125.3, 125.1, 124.4, 119.6, 115.1, 55.9. MS:m/e 420.

EXAMPLE 14

2-(4-Cyanophenyl)-4-(2-methoxy-4-cyanophenyl)pyrimidine

A suspension of the dibromo compound of Example 13 (8.4 g, 0.02 mole) and copper(I)cyanide (4.45, 0.05 mole) in 40 mL dry DMF is heated at reflux under nitrogen for 30 hr (TLC followed). The excess DMF is distilled under vacuum and the residue triturated with 100 mL water and stirred with 500 mL 10% sodium cyanide (aqueous) for 1 hr, filtered, washed with water and dried. The solid is subjected to soxlet extraction with acetone (24 hr) followed by chromatography over neutral aluminumoxide, elution with ether:$CHCl_3$ (8:2) to chloroform, to yield a white crystalline solid. Recrystallized from $CHCl_3$:ether (1:4) yielded 2.5 g of a white solid (40%) having a mp 239°–240° C.

Characterization: IR (KBR) 3085, 2229, 1579, 1556, 1406, 1274, 1027, 819 $cm^1$. $^1H$ NMR ($CDCl_3$) 8.88 (d, III, j=4.4), 8.65 (d, 2H, j=8.3), 8.3 (d, 2H, j=8.3), 7.94 (d, 1H, j=4.4), 7.79 (d, 2H, j=8.3), 7.46 (dd, IH, J=8.3, J=1.4), 7.3(s, 1H), 3.99 (s, 3H). $^{13}C$ NMR ($CDCl_3$) 162.9, 161.0, 158.1, 157.6, 141.7, 132.3, 132.0, 130.5, 124.9, 120.6, 118.7, 118.2, 115.0, 114.2, 56.2. MS:m/e 312. Analysis calculated for $C_{19}H_2N_4O$: C: 73.06, H: 3.87, N: 17.93; found: C: 72.93, H: 3.81, N: 17.88.

EXAMPLE 15

2-(4-[Imidazolin-2-yl]phenyl)-4-(2-methoxy-4-[imidazolin-2-yl]phenyl)pyrimidine

A stirred suspension of dinitrile (0.003 mole, 0.93 g) in 80 mL absolute ethanol is saturated with dry HCl gas at 0° C. and stirred for 3 days. The reaction mixture is diluted with 200 mL dry ether and the solid filtered, washed with dry ether, and dried in vacuum for 6 hr to obtain 1.3 g (85%). The imidate ester (0.77 g, 0.002 mole) in 20 mL dry ethanol and ethylene diamine (0.35 g, 0.006 mole) is heated at gentle reflux for 12 hr and the solvent is removed by distillation. The residue is diluted with 30 mL water and basified with 1N NaOH to pH 10 with external cooling. The white solid is filtered, washed with water, dried and recrystallized from hot ethanol to yield 0.58 g (74%) with a mp of 150°–151° C.

Characterization: IR(KBr) 3375, 3214, 2938, 2866, 1606, 1567, 1429, 1275, 1233, 1027, 986 $cm^{-1}$. $^1H$ NMR (DMSO $d_6$/45° C.) 8.93 (d, 1H, j=5.4), 8.51 (d, 2H, j=8.3), 8.21 (d, 1H, j=7.8), 8.0 (d, 2H, j=7.8), 7.98 (d, 1H, j=2.4), 7.67 (s, 1H), 7.63 (d, 2H, j=7.8), 3.97 (s, 3H), 3.67 (s, 4H), 3.65 (s, 4H). $^{13}C$ NMR (DMSO $d_6$/45° C.) 163.2, 163.0, 162.7, 161.4, 157.6, 157.5, 138.8, 134.0, 132.50, 130.3, 127.4, 127.3, 126.7, 119.7, 119.5, 110.8, 55.8, 49.5. Ms m/e 398.

The free base (0.4 g, 0. 001 mole) in 10 mL ethanol and 10 mL ethanolic HCl is heated under reflux for 1 hr, the excess solvent is distilled under vacuum, triturated with dry ether, and the precipitated solid is filtered, washed with dry ether, and dried in vacuum at 75° C. for 12 hr to yield 0.42 g (844).

Characterization: IR(KBr) 3361 (br), 3113, 1617, 1590, 1258, 1024, 791 $cm^{-1}$. $^1H$ NMR ($D_2O$/DMSO$d_6$/45° C.) 8.78 (d, 1H, j=4.9), 8.3 (d, 2H, j=6.9), 8.08 (d, 1H, j=5.8), 7.98 (d, 1H, j=5.3), 7.88 (d, 2H, j=6.8), 7.44 (d, 1H, j=8.3), 7.42 (s, 1H), 4.1 (s, 4H), 4.08 (s, 4H). $^{13}C$ NMR ($D_2O$/DMSO$d_6$) 166.3, 166.0, 162.7, 162.0, 159.6, 159.0, 143.2, 132.8, 130.8, 129.8, 126.1, 124.8, 122.1, 121.7, 112.8, 57.5, 45.9. Analysis calculated for $C_{23}H_{22}N_6$·$3HCl$·$5H_2O$: C: 51.64, H: 5.27, N: 15.71; found: C: 51.33, H: 5.41, N: 15.63.

EXAMPLE 16

2-(4-[Guanyl]phenyl)-4-(2-methoxy-4-[guanyl]phenyl)pyrimidine

The dinitrile (0.85 g, 0.0027 mole) is suspended in 35 mL of absolute ethanol and saturated with dry HCl at 0° C. and stirred for 4–5 days at room temperature. The imidate ester, a white precipitate (1.2 g, 0.0023 mole), is filtered and dried in vacuum. The dry solid is suspended in 30 mL of absolute ethanol, saturated with dry ammonia, and stirred for 2 days. The solvent is removed under vacuum and the residue suspended in ice-water, basified with 1N NaOH to pH 10, and the precipitate filtered, dried and crystallized from ethanol to yield 0.68 g (73%) of a white cyrstalline solid having a mp 148°–149° C.

Characterization: IR(KBr) 3380, 3290, 3212, 1645, 1570, 1420, 1420, 1256, 1185, 1026, 829 $cm^{-1}$. $^1H$ NMR (DMSO$d_6$/$D_2O$) 8.84 (d, 1H, j=4.4), 8.42 (d, 2H, j=8.4), 8.09 (d, 1H, j=4.4), 7.9 (d, 1H, j=5.2), 7.66 (d, 2H, j=8.4), 7.53 (brd, 1H), 7.47 (d, 1H, j=8.8). $^{13}C$ NMR (DMSO$d_6$/$D_2O$) 163.8, 163.5, 163.3, 162.2, 158.3, 158.2, 139.8, 139.4, 138.2, 131.1, 128.2, 127.6, 127.3, 120.5, 119.7, 111.1, 56.5. MS m/e 346.

The free base (0.55 g, 0.0016 mole) in 10 mL absolute ethanol is saturated with dry HCl, stirred at room temperature for 5–6 hr, diluted with dry ether, and the resultant precipitate filtered, dried in vacuum for 12 hr at 80° C., to yield 0.65 g (75%) with a mp of 255°–257° C.

Characterization: IR(KBr) 3380, 3270, 3137, 1677, 1597, 1257, 1019, 735 $cm^{-1}$. $^1H$ NMR (DMSO$_d$) 9.79 (s, 2H), 9.65 (s, 2H), 9.49 (s, 2H), 9.44 (s, 2H), 9.0 (d, 1H, j=6.8), 8.6 (d, 2H, j=8.4), 8.25 (d, 1H, j=8.0), 8.04 (m, 3H), 7.77 (s, 1H), 7.67 (d, 1H, j=8.0). $^{13}C$ NMR (DMSO$d_6$) 165.4, 164.9, 162.1, 161.0, 158.2, 157.6, 141.8, 131.1, 130.9, 129.8 129.7, 128.7, 120.0, 120.7, 120.5, 112.4, 56.6. Analysis calculated for $C_{19}H_{18}N_6O$·$3HCL$·$1.5H_2O$: C: 47.26, H: 5.01, N: 17.4; found: C: 47.26, H: 5.21, N: 17.18.

EXAMPLE 17

2-(4-[N-i-Propylguanyl]phenyl)-4-(2-methoxy-4-[N-i-propylguanylphenyl)pyrimidine Distilled isopropyl amine (0.44 g, 0.00075 mole) is added to a suspension of the imidate ester (1.4 g, 0.0025 mole) in 20 mL absolute ethanol. After 3 hr of stirring the solution becomes clear; stirring is continued overnight at room tempture. The excess ethanol in distilled water is added, and the solid which separated is filtered, washed with deionized water, dried and recrystallized from ethanol:ether (1:3) to yield 0.80 g (75%), mp 179°–180° C.

Characterization: IR(KBr) 3257, 3058, 2966, 1597, 1566, 1429, 1386, 1251, 1183, 801 $cm^{-1}$. $^1H$ NMR (DMSO$d_6$/$D_2O$) 8.9 (d, 1H, j=4.9), 8.46 (d, 2H, j=8.5), 8.12 (d, 1H, j=8.5), 7.94 (d, 1H, j=5.5), 7.85 (d, 2H, j=8.5), 7.48 (s, 1H), 7.46 (d, 1H, j=4.9), 3.96 (s, 3H) 3.82 (brm, 2H), 1.15 (d, 6H, j=6.7), 1.13 (d, 6H, j=6.1). $^{13}C$ NMR (DMSO$d_6$/$D_2O$) 162.8, 161.6, 157.5, 157.2, 157.1, 141.0, 139.3, 138.2, 130.0, 127.2, 126.8, 126.0, 119.5, 119.1, 110.4, 55.8, 43.7, 22.8. MS m/e 430.

Free base (0.66 g, 0.0015 mole) in 5 mL ethanol and 10 mL ethanol HCl is heated for 30 min, the excess ethanol is distilled, the residue is diluted with dry ether (50 mL), filtered, washed with dry ether, and dried in vacuum at 60° C. (12 hr) to yield 0.75 g (79%) mp 224°–226° C.

Characterization: IR (KBr) 3422, 3218, 3068, 1667, 1619, 1571, 1394, 1264, 1129, 1003, 738 cm$^{-1}$. $^1$H NMR (D$_2$O/DMSO/45° C.) 8.95 (d, 1H, j=5.4), 8.55 (d, 2H, j=8.3), 8.18 (d, 1H, j=8.79), 8.0 (d, 1H, j=5.4), 7.83 (d, 2H, j=8.3), 7.45 (s, 1H), 7.44 (d, 1H, j=5.4 ), 3.96 (br, 2H), 3.89 (s, 3H), 1.29 (d, 6H). $^{13}$C NMR (D$_2$O/DMSO/45° C.) 163.0, 162.4, 162.1, 158.9, 158.3, 142.0, 132.74, 131.9, 131.9, 131.5, 130.1, 129.3, 128.8, 121.4, 121.2, 112.6, 57.0, 46.0, 46.0, 21.6. Analysis calculated for C$_{25}$H$_{30}$N$_6$O•3HCl•H$_2$O: C: 54.00, H: 6.34, N: 15.32; found: C: 53.87, H: 6.41, N: 15.46.

EXAMPLE 18

5-Methyl-2,4-bis(4-bromophenyl)pyrimidine

A mixture of 4-bromopropiophenone (21.3 g, 0.1 mole) and N,N-dimethylformamide dimethyl acetal (23.8 g, 0.2 mole) is refluxed for 6–7 hr with careful distillation of the methanol produced by the reaction, and the excess DMF-acetal is distilled. The residual mass is subjected to vaccumm distillation to yield 18.7 g (70%) of a dark brown thick oil which solidifies on standing, mp 37°–42° C.

Characterization: $^1$H NMR (CDCl$_3$) 7.47 (d, 2H, j=8.3), 7.28 (d, 2H, j=8.3), 6.82 (s, 1H), 3.05 (s, 6H), 2.11 (s, 3H). $^{13}$C NMR (CDCl$_3$) 195.3, 156.4, 142.7, 130.9, 129.8, 123.1, 105.8, 43.1, 10.9. MS: m/e 268.

Sodium ethoxide (0.06 mole), (prepared from 1.38 g sodium in 75 mL absolute ethanol) is gradually added to a stirred suspension of p-bromobenzamidine benzenesulfonate (10.7 g, 0.03 mole), and 3-dimethylamino-1-(4-bromobenzoyl)-2-methylpropen-1-one (8.04 g, 0.03 mole) in 75 mL absolute ethanol, and the reaction mixture is heated under reflux for 12–16 hr (TLC monitored). Solvent is distilled and the residue is treated with 150 mL water. The resulting solid is filtered, washed with water and dried. The product is dissolved in 250 mL chloroform, dried over anhydrous sodium sulfate, filtered, concentrated and recrystallized from chloroform:ether (1:4) to yield 7.75 g (64%) of a white crystallized solid, mp 136°–137° C.

Characterization: IR(KBr) 2381, 2346, 1588, 1533, 1484, 1429, 1099, 1009, 858, 756 cm$^{-1}$. $^1$H NMR (CDCl$_3$) 8.63 (s, 1H), 8.34 (d, 2H, j=8.8), 7.63 (d, 2H, j=8.8), 7.57 (d, 4H, j=8.8), 2.37 (s, 3H). $^{13}$C NMR (CDCl$_3$) 163.8, 161.7, 159.5, 137.1, 136.5, 131.6, 130.7, 129.6, 125.7, 125.1, 124.0, 17.0. MS: m/e 404.

EXAMPLE 19

5-Methyl-2,4-bis(4-cyanophenyl)pyrimidine

A mixture of 5-methyl-2,4-bis(4-bromophenyl)pyrimidine (8.08 g, 0.02 mole) and copper(I) cyanide (4.45 g, 0.05 mole) in 35 mL dry DMF is refluxed under nitrogen for 40 hr (TLC monitored), the excess DMF is distilled under vacuum using a water aspirator. The residual mass is diluted with water and poured into 200 mL 10% NaCN solution, stirred for 2–3 hr, filtered, washed thoroughly with water, dried and subjected to soxlet extraction using acetone. The acetone is distilled and the residue dissolved into 75 mL CHCl$_3$ and chromatographed over an aluminumoxide column, eluted with ether to 80:20 CHCl$_3$:ether to yield a white crystalline solid (2.8 g, 48%), mp 194°–195° C.

Characterization: IR(KBr) 2226, 1608, 1581, 1509, 1426, 1211, 1110, 1073, 971, 906, 794 cm$^{-1}$. $^1$H NMR (CDCl$_3$ 8.78 (s, 1H), 8.6 (d, 2H, j=8.3), 8.3 (4H), 7.77 (d, 2H, j=8.3), 2.45 (s, 3H). $^{13}$C NMR (CDCl$_3$) 163.2, 160.9, 160.0, 142.2, 141.3, 132.3, 132.2, 129.7, 128.5, 126.9, 118.7, 118.3, 113.9, 113.4, 16.9. MS: m/e 296. Analysis calculated for C$_{19}$H$_{12}$N$_4$: C: 77.0, H: 4.08, N: 18.90; found: C: 69.92, H: 4.11, N: 18.86.

EXAMPLE 20

5-Methyl-2,4-bis-(4-[imidazolin-2-yl]phenyl)pyrimidine

The dinitrile (0.0025 mole, 0.75 g) in 40 mL absolute ethanol is saturated with dry HCl gas at 0° C., stirred at room temperature for 3–4 hr, and monitored by disappearance of nitrile adsorption by IR. The reaction mixture is diluted with dry ether (100 mL), filtered, and the white solid is washed with dry ether and dried in vacuum for 3–4 hr to yield 1.1 g (89%). The imidate ester 1.1 g (0.0022 mole) is suspended in 25 mL absolute ethanol, ethylenediamine (0.39 g, 0.003 mole) is added, and the mixture is allowed to reflux for 12 hr. The excess solvent is distilled and the residue triturated with ice cold water (50 mL) and basified while cooling and stirring with 1N NaOH to pH 10). The resulting solid is filtered and washed with water, dried and crystallized from ethanol:ether to yield 0.63 g (75%) mp 127°–129° C.

Characterization: IR(KBr) 3392, 3288, 3166, 2971, 1602, 1549, 1421, 1278, 1168, 990, 855, 801 cm$^{-1}$. $^1$H NMR (DMSOd$_6$/35° C.) 8.85 (s, 1H), 8.44 (d, 2H, j=8.5), 7.98 (t, 4H), 7.83 (d, 2H, j=6.9), 3.66 (s, 4H), 3.64 (s, 4H), 2.4 (s, 3H). $^{13}$C NMR (DMSOd$_6$/35° C.) 163.5, 163.4, 163.3, 160.5, 159.6, 139.6, 139.0, 131.3, 130.6, 128.9, 127.5, 127.1, 126.6, 49.1, 49.0, 16.4. MS: m/e 382.

A solution of 0.38 g (0.001 mole) free base in 10 mL absolute ethanol is treated with 5 mL saturated ethanolic HCl, and the mixture is heated under reflux for 20 min. The mixture is cooled and diluted with 75 mL dry ether, and the white precipitated obtained is filtered, washed with ether, and dried in vacuum for 12 hr at 60°–70° C. to yield 0.48 g (83%), mp 244°–245° C.

Characterization: IR (KBr) 3446, 3108, 2954, 1600, 1377, 1284, 1071, 853 cm$^{-1}$. $^1$H NMR (DMSOd$_6$/45° C.) 9.0 (s, 1H), 8.61 (d, 2H, j=8.4), 8.39 (d, 2H, j=8.4), 8.32 (d, 2H, j=8.4), 8.08 (d, 2H, j=8.4), 5.12 (br s, 5H), 4.08 (s, 4H), 4.06 (s, 4H), 2.46 (s, 3H). $^{13}$C NMR (DMSOd$_6$/45° C.) 164.2, 164.1, 162.8, 160.13, 159.8, 142.9, 142.1, 129.7, 129.3, 128.9, 127.9, 123.7, 123.73, 122.9, 44.3, 16.4. Analysis calculated for C$_{23}$H$_{22}$N$_6$•3HCl•H$_2$O: C: 54.17, H: 5.33, N: 10.48; found: C: 53.91, H: 5.46, N: 10.38.

EXAMPLE 21

2-(4-Bromobenzyl)-4-bromophenyl)pyrimidine

A solution of 4-bromophenylacetonitrile (52 g, 0.25 mole) in 50 mL absolute ethanol and 200 mL dry ether is saturated with dry HCl gas at 0° C. Considerable solid precipitates, the suspension is stirred vigorously for two days at room temperature, 200 mL dry ether is added, and the imidate ester is filtered, washed with dry ether and dried in vacuo at 25° C. to yield 50.0 g (75%).

Dry ammonia gas is bubbled, until saturation, to a stirred suspension of the above imidate ester (50 g, 0.189 mole) in 100 mL absolute ethanol at 0° C. The mixture is allowed to stir at 0° C. for 4–5 hr and then for two days at room temperature. The excess ammonia and ethanol are removed in vacuo, the oil diluted with water and basified with 1M NaOH to ca. pH 10. An oil separates and it is extracted with 200 mL chloroform, dried ($Na_2SO_4$), and the solvent is evaporated. The solid is recrystallized from $CHCl_3$:ether (1:4) to yield 33 g (77.5%), mp 125°–126° C.

Characterization: IR (KBr) 3436, 3313, 3138, 3056, 2936, 1638, 1607, 1489, 1441, 1419, 1167, 1070, 1013, 799, 746, 496 $cm^{-1}$. $^1H$ NMR ($CDCl_3$/DMSO-$d_6$) 7.58 (s, 2H, 7.42 (d, 2H, j=8.1), 7.14 (d, 2H, j=8.1), 5.42 (br s, 1H), 3.44 (s, 2H). $^{13}C$ NMR ($CDCl_3$/DMSO-$d_6$) 165.4, 134.4, 130.8, 130.3, 119.9, 77.2. MS m/e 225.

To a stirred mixture of 4-bromophenylacetamidine (11.25 g, 0.04 mole) and 1-dimethylamino-3-dimethylimonio-1-(4-bromophenyl)-1-propane perchlorate (15.25 g, 0.04 mole) in 100 mL of dry ethanol is added 0.04 mole sodium ethoxide (prepared from 0.92 g Na and 65 mL ethanol). After stirring for 30 min at room temperature a further equivalent of sodium ethoxide is added, and the mixture is heated under reflux for 2 hr. The solvent is removed under reduced pressure, and the yellow-brown residue triturated with 150 mL water. The solid is filtered, washed with water, dried in air and recrystallized from ether:hexane (1:3) to give 12.5 g (77%) of a pale yellow crystalline solid, mp 93°–94° C.

Characterization: IR(KBr) 3031, 1587, 1569, 1541, 1486, 1440, 1381, 1064, 1013, 811, 770 $cm^{-1}$. $^1H$ NMR ($CDCl_3$, 35° C.) 8.67 (d, 1H, j=5.4), 7.93 (d, 2H, j=8.3), 7.6 (d, 2H, j=8.79), 7.45 (d, 1H, j=5.4), 7.41 (d, 2H, j=8.3), 7.28 (d, 2H, j=8.3), 4.27 (s, 2H). $^{13}C$ NMR ($CDCl_3$, 35° C.) 169.5, 162.9, 158.0, 137.2, 135.5, 132.1, 131.5, 130.9, 128.6, 125.7, 120.5, 113.9, 45.4. MS m/e 403 (M+−1, 100%), 404 (M+, 90%).

EXAMPLE 22

2-(4-Cyanobenzyl)-4-(4-cyanophenyl)pyrimidine

A mixture of 2-(4-bromobenzyl)-4-(4-bromophenyl)pyrimidine (8.8 g, 0.02 mole) and copper(I) cyanide (4.45 g, 0.05 mole) in 25 mL dry N-methyl-2-pyrrolidone is heated under nitrogen for 3–4 hr (TLC followed), during which time the color changes to dark brown. The mixture is poured into 250 mL ice cold water and a brown solid precipitated. The mixture is stirred for 2 hr with 200 mL of 10% NaCN solution; the solid is filtered, washed with water (1 L) and dried. The brown solid is placed in a soxlet device and treated with ethanol for 36 hr. The solvent is removed, the light brown solid chromatographed over neutral aluminumoxide, elution is with ether:$CHCl_3$ (8:2) (20×50 mL fractions). Evaporation of the solvent yields a white solid which is dried in vacuo at 100° C. for 6–7 hr to give 2.3 g (39%), mp 155°–156° C.

Characterization: IR(KBr) 3059, 2220, 1611, 1569, 1541, 1440, 1376, 857, 820, 770, 687 $cm^{-1}$. $^1H$ NMR ($CDCl_3$, 35° C.): 8.8 (d, 1H, j=5.4), 8.19 (d, 2H, j=8.8), 7.8 (d, 2H, j=8.8), 7.61 (d, 2H, j=8.3), 7.60 (d, 1H, j=5.4), 7.53 (d, 2H, j=8.3), 4.42 (s, 2H). $^{13}C$ NMR ($CDCl_3$, 35° C.): 169.0, 162.1, 158.6, 143.4, 140.5, 132.6, 132.2, 130.0, 127.7, 118.8, 118.2, 114.8, 114.5, 110.6, 45.92. MS m/e 295. Analysis calculated for $C_{19}H_{12}N_4$: C: 77.00, H: 4.08, N: 18.90; found: C: 69.88, H: 4.12, N: 18.79.

EXAMPLE 23

2-[4-(2-imidazolinyl)benzyl]-4[(2-imidazolinyl)phenyl]pyrimidine

The bis-nitrile (2.9 g, 0.01 mole) is suspended in 150 mL absolute ethanol, cooled in an ice-salt bath and treated with dry HCl gas. The compound dissolves to give a clear yellow solution which is stirred at room temperature in a closed flask for 24 hr. The imidate ester hydrochloride which precipitates is filtered and washed with 150 mL of dry ether. A second crop of imidate ester hydrochloride is obtained from the filtrate. The two precipitates are combined and dried in vacuo at 25° C. for 4–5 hr to yield 3.65 g (74%).

The bisimidate ester hydrochloride (1.98 g, 0.004 mole) is suspended in 25–30 mL absolute ethanol, ethylene diamine (dried by distilling from sodium) (0.6 g, 0.01 mole) is added, and the mixture is heated under reflux for 12 hr. The solvent is removed in vacuo and the resulting solid is triturated with water, basified while cooling with 1N NaOH to ca. pH 10, and the white precipitate thus obtained is filtered, washed thoroughly with water, dried and recrystallized from hot ethanol to yield 1.14 g (75%), mp 210° C.

Characterization: IR(KBr) 3383, 3134, 2971, 1619, 1600, 1566, 1432, 1408, 1389, 1205, 982, 829 $cm^{-1}$. $^1H$ NMR (DMSO-$d_6$/60°) 8.79 (d, 1H, j=5.5), 8.21 (d, 2H, j=8.6), 7.96 (d, 2H, j=8.6 ), 7.91 (d, 1H, j=5.5), 7.75 (d, 2H, j=7.9), 7.40 (d, 2H, j=7.9), 4.32 (s, 2H), 3.64 (s, 4H), 3.58 (s, 4H). $^{13}C$ NMR (DMSO-$d_6$/60° C.) 168.5, 164.1, 163.2, 161.9, 158.9, 143.2, 138.2, 131.0, 129.4, 127.9, 127.8, 126.8, 124.0, 114.8, 48.4, 46.5, 44.9. MS m/e 381.

The free base (1.0 g, 0.0026 mole) is suspended in 20 mL saturated ethanolic HCl and refluxed for 2 hr. The solvent is distilled and the residue treated with dry ether. The precipitated salt is filtered, washed with ether, and dried in vacuo at 80° C. for 24 hr to yield 0.95 g (73%), mp 215°–218° C. (dec.).

Characterization: IR(KBr) 3431, 3086, 2952, 1619, 1590, 1562, 1504, 1442, 1361, 1274, 1626, 992, 825, 686 $cm^{-1}$. $^1H$ NMR (DMSO-$d_6$/65° C.) 11.14 (s, 1H), 10.84 (s, 1H), 8.87 (d, 1H, j=5.4), 8.38 (d, 2H, j=7.32), 8.30 (d, 1H, j=5.4), 8.29 ( d, 2H, j=8.3), 8.05 (d, 2H, j=8.3), 7.62 (d, 2H, j=7.3), 4.45 (s, 2H), 4.02 (s, 4H), 3.97 (s, 4H). Analysis calculated for $C_{23}H_{22}N_6 \cdot 3HCl \cdot 0.5H_2O$: C: 55.15, H: 5.23, N: 16.78; found: C: 55.31, H: 5.44, N: 16.56.

EXAMPLE 24

2(4-[tetrahydropyrimidinyl-2-yl]benzyl-4-(4-[tetrahydropyrimidinyl-2-yl]phenylpyrimidine Freshly distilled, 3-diaminopropane (0.74 g, 0.01 mole) is added to a suspension of bis-imidate ester hydrochloride (1.98 g, 0.0004 mole) in 30 mL absolute ethanol and refluxed for 12 hr. Solvent is distilled under vacuum, the resisdue is triturated with ice/water, basified with 1N NaOH to pH 10, and the precipitated solid is filtered, washed with water, dried and recrystallized from ethanol to yield 1.0 g (63%) of an off-white solid, mp 225°–226° C.

Characterization: IR(KBr) 3353, 3179, 2943, 1618, 1575, 1438, 1367, 1317, 1196, 832 $cm^{-1}$. $^1H$ NMR (DMSO$d_6$) 8.77 (d, 1H, j=5.4), 8.17 (d, 2H, j=8.8), 7.90 (d, 1H, j=5.4), 7.89 (d, 2H, j=8.79), 7.67 (d, 2H, j=8.3), 7.42 (d, 2H, j=8.3), 4.3 (s, 2H), 3.4-3.35 (m, 8H), 1.8-1.72 (m, 4H). $^{13}C$ NMR (DMSO$d_6$) 168.8, 162.2, 158.5, 155.7, 153.0, 141.5, 140.2, 138.0, 136.9, 131.1, 129.0, 126.7, 126.5, 114.6, 44.9, 41.2, 20.1, 19.2. MS: m/e 410.

The free base (0.92 g, 0.002 mole) in 20 mL ethanolic HCl is refluxed for 2–3 hr, the excess alcohol distilled and the residue triturated with dry ether. The solid thus obtained is filtered, washed with ether and dried under vacuum for 12 hr at 80° C. to yield 0.9 g (75%) of an off-white crystalline solid, mp 247°–248° C.

Characterization: IR(KBr) 3425, 3271, 3179, 1620, 1574, 1440, 11376, 1317, 832 cm$^{-1}$. $^1$H NMR (DMSOd$_6$) 11.18 (s, 2H), 10.9 (s, 2H), 8.9 (d, 1H, j=5.5), 8.4 (d, 2H, j=8.55), 8.31 (d, 2H, j=8.55), 8.09 (d, 1H, j=5.5), 8.08 (d, 2H, j=8.5), 7.62 (d, 2H, j=8.5), 4.32 (s, 2H). Analysis calculated for $C_{25}H_{26}N_6 \cdot 3HCl \cdot 1.5H_2O$: C: 54.89, H: 5.71, N: 15.36 ; found: C: 54.67, H: 5.88, N: 15.43.

The foregoing is illustrative of the present invention and is not to be construed as limiting thereof. The invention is defined by the following claims, with equivalents of the claims to be included therein.

That which is claimed is:

1. A method of treating *Cryptosporidium parvum* in a subject in need of such treatment, comprising administering to said subject a compound of Formula I:

(I)

wherein:

X and Y are located in the para or meta positions and are each wherein:

each $R_1$ is independently selected from the group consisting of H, loweralkyl, alkoxyalkyl, hydroxyalkyl, aminoalkyl, alkylaminoalkyl, cycloalkyl, aryl, or alkylaryl or two $R_1$ groups together represent $C_2$-$C_{10}$ alkyl, hydroxyalkyl, or alkylene, or two $R_1$ groups together represent wherein m is from 1–3 and $R_7$ is H or -CONHR$_8$NR$_9$R$_{10}$, wherein $R_8$ is loweralkyl, and $R_9$ and $R_{10}$ are each independently selected from the group consisting of H and lower alkyl;

$R_2$ is H, hydroxy, loweralkyl, alkoxyalkyl, hydroxyalkyl, aminoalkyl, alkylaminoalkyl, cycloalkyl, aryl, or alkylaryl;

n is a number from 0 to 2;

$R_3$ and $R_4$ are each independently selected from the group consisting of H, loweralkyl, loweralkoxy, alkylaryl, aryl, oxyaryl, aminoalkyl, aminoaryl, or halogen; and $R_5$ and $R_6$ are each independently selected from the group consisting of H, loweralkyl, aryl, alkylaryl, aminoalkyl, aminoaryl, halogen, oxyalkyl, oxyaryl, or oxyarylalkyl;

or a pharmaceutically acceptable salt thereof, in an amount effective to treat *Cryptosporidium parvum*.

2. A method of treating *Cryptosporidium parvum* in a subject in need of such treatment, comprising administering to said subject a compound of Formula I:

(I)

wherein:

X and Y are located in the para or meta positions and are each wherein:

each $R_1$ is H, $R_2$ is H, n is 0, $R_3$ is H, $R_4$ is H, $R_5$ is H, and $R_6$, is H;

or a pharmaceutically acceptable salt thereof, in an amount effective to treat *Cryptosporidium parvum*.

3. A method of treating *Cryptosporidium parvum* in a subject in need of such treatment, comprising administering to said subject a compound of Formula I:

(I)

wherein:

X and Y are located in the para or meta positions and are each wherein:

two $R_1$ groups together represent $C_2$ alkylene, $R_2$ is H, n is 0, $R_3$ is H, $R_4$ is H, $R_5$ is H, and $R_6$ is H;

or a pharmaceutically acceptable salt thereof, in an amount effective to treat *Cryptosporidium parvum*.

4. A method of treating *Cryptosporidium parvum* in a subject in need of such treatment, comprising administering to said subject a compound of Formula I:

(I)

wherein:

X and Y are located in the para or meta positions and are each $$-C\overset{NR_1}{\underset{\underset{R_2}{|}}{\diagdown}}_{NR_1}$$

wherein:
two $R_1$ groups together represent $C_3$ alkylene, $R_2$ is H, n is 0, $R_3$ is H, $R_4$ is H, $R_5$ is H, and $R_6$ is H;
or a pharmaceutically acceptable salt thereof, in an amount effective to treat *Cryptosporidium parvum*.

5. A method of treating *Cryptosporidium parvum* in a subject in need of such treatment, comprising administering to said subject a compound of Formula I:

(I) [structure showing pyrimidine with $R_3$, $R_5$, $R_6$, $R_4$, X, Y substituents and $(CH_2)_n$ linkers]

wherein:
X and Y are located in the para or meta positions and are each $$-C\overset{NR_1}{\underset{\underset{R_2}{|}}{\diagdown}}_{NR_1}$$

wherein:
each $R_1$ is H, $R_2$ is loweralkyl, n is 0, $R_3$ is H, $R_4$ is H, $R_5$ is H, and $R_6$ is H;
or a pharmaceutically acceptable salt thereof, in an amount effective to treat *Cryptosporidium parvum*.

6. A method of treating *Cryptosporidium parvum* in a subject in need of such treatment, comprising administering to said subject a compound of Formula I:

(I) [structure]

wherein:
X and Y are located in the para or meta positions and are each $$-C\overset{NR_1}{\underset{\underset{R_2}{|}}{\diagdown}}_{NR_1}$$

wherein:
each $R_1$ is H, $R_2$ is H, n is 0, $R_3$ is H, $R_4$ is loweralkoxy, $R_5$ is H, and $R_6$ is H;
or a pharmaceutically acceptable salt thereof, in an amount effective to treat *Cryptosporidium parvum*.

7. A method of treating *Cryptosporidium parvum* in a subject in need of such treatment, comprising administering to said subject a compound of Formula I:

(I) [structure]

wherein:
X and Y are located in the para or meta positions and are each $$-C\overset{NR_1}{\underset{\underset{R_2}{|}}{\diagdown}}_{NR_1}$$

wherein:
two $R_1$ groups together represent $C_2$ alkylene, $R_2$ is H, n is 0, $R_3$ is H, $R_4$ is loweralkoxy, $R_5$ is H, and $R_6$ is H;
or a pharmaceutically acceptable salt thereof, in an amount effective to treat *Cryptosporidium parvum*.

8. A method of treating *Cryptosporidium parvum* in a subject in need of such treatment, comprising administering to said subject a compound of Formula I:

(I) [structure]

wherein:
X and Y are located in the para or meta positions and are each $$-C\overset{NR_1}{\underset{\underset{R_2}{|}}{\diagdown}}_{NR_1}$$

wherein:
two $R_1$ groups together represent $C_3$ alkylene, $R_2$ is H, n is 0, $R_3$ is H, $R_4$ is loweralkoxy, $R_5$ is H, and $R_6$ is H;
or a pharmaceutically acceptable salt thereof, in an amount effective to treat *Cryptosporidium parvum*.

9. A method of treating *Cryptosporidium parvum* in a subject in need of such treatment, comprising administering to said subject a compound of Formula I:

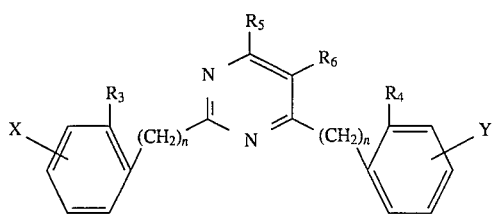
wherein:
X and Y are located in the para or meta positions and are each
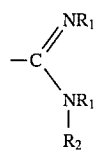
wherein:
each $R_1$ is H, $R_2$ is

UNITED STATES PATENT AND TRADEMARK OFFICE
CERTIFICATE OF CORRECTION

PATENT NO. : 5,622,955

DATED : April 22, 1997

INVENTOR(S) : D. Boykin et al.

It is certified that error appears in the above-identified patent and that said Letters Patent is hereby corrected as shown below:

On the title page, item:

[56], Other Publications, third Das reference, replace "Snythesis" with --Synthesis--.

Col. 3, line 17, replace "loweralkoxy" with --"loweralkoxy"--.

Col. 4, line 35, replace "complex) ," with --complex),--.

Col. 7, replace the middle two strings of Scheme 1 with the following:

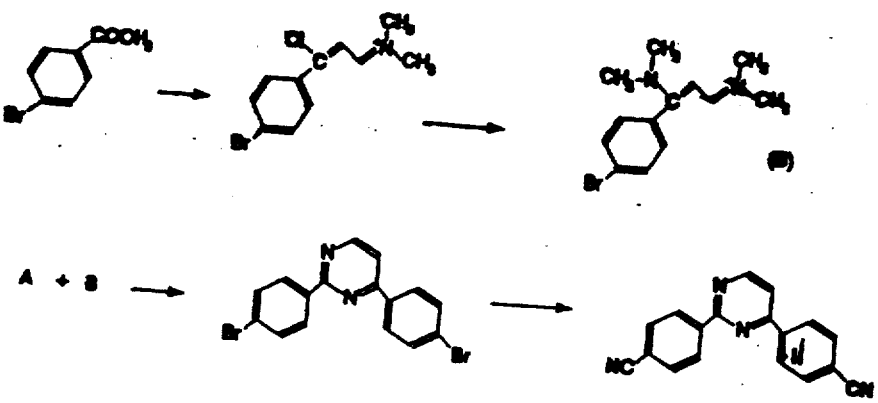

UNITED STATES PATENT AND TRADEMARK OFFICE
CERTIFICATE OF CORRECTION

PATENT NO. : 5,622,955
DATED : April 22, 1997
INVENTOR(S) : D. Boykin et al.

It is certified that error appears in the above-identified patent and that said Letters Patent is hereby corrected as shown below:

Col. 15, line 60, replace "(844)" with --(84%)--
Col. 25, line 23, replace "pharmaceumically" with --pharmaceutically--.

Signed and Sealed this

Twelfth Day of August, 1997

Attest:

BRUCE LEHMAN

*Attesting Officer*    Commissioner of Patents and Trademarks